United States Patent [19]
Sato et al.

[11] Patent Number: 5,640,462
[45] Date of Patent: Jun. 17, 1997

[54] IMAGING METHOD OF X-RAY COMPUTERIZED TOMOGRAPHY AND APPARATUS FOR X-RAY COMPUTERIZED TOMOGRAPHY

[75] Inventors: Katsutoshi Sato, Hitachi; Shigeru Izumi, Tokyo; Shoji Kamata, Yokohama; Hiroshi Miyai, Hitachi; Hiroshi Kitaguchi, Naka-machi; Masahiro Kondo, Hitachi; Seishi Watahiki, Katsuta, all of Japan

[73] Assignee: Hitachi, Ltd., Tokyo, Japan

[21] Appl. No.: 945,903

[22] Filed: Sep. 17, 1992

[30] Foreign Application Priority Data

Sep. 17, 1991 [JP] Japan ................... 3-265227

[51] Int. Cl.$^6$ ................................................ G06K 9/00
[52] U.S. Cl. ..................... 382/131; 382/132; 382/270
[58] Field of Search ............................ 382/6, 18, 54, 382/8, 128, 131, 132, 275, 270, 274; 364/413.19, 20, 22, 23; 378/95, 99, 4, 22

[56] References Cited

U.S. PATENT DOCUMENTS

| | | | |
|---|---|---|---|
| 4,219,876 | 8/1980 | Mizutani et al. | 364/414 |
| 4,289,969 | 9/1981 | Cooperstein et al. | 250/445 T |
| 4,433,380 | 2/1984 | Abele et al. | 364/414 |
| 4,670,892 | 6/1987 | Abele et al. | 378/4 |
| 4,809,312 | 2/1989 | Annis | 378/146 |
| 4,878,169 | 10/1989 | Toner et al. | 364/413.19 |
| 4,922,915 | 5/1990 | Arnold et al. | 128/653 R |
| 5,034,969 | 7/1991 | Ozaki | 378/18 |
| 5,068,788 | 11/1991 | Goodenough et al. | 364/413.14 |

FOREIGN PATENT DOCUMENTS

58-46947  3/1983  Japan .

*Primary Examiner*—Joseph Mancuso
*Attorney, Agent, or Firm*—Antonelli, Terry, Stout & Kraus, LLP

[57] ABSTRACT

An imaging method of an X-ray computerized tomography (X-ray CT) comprising the steps of reconstructing a partial region including a region of interest from penetrating data of an object, extracting only shape information from the reconstructed image, setting a threshold function determined by resolution to the reconstructed image information which is equivalent to linear absorption coefficient distribution (density), extracting the reconstructed image information by making the information into bi-values or tri-values based on the threshold function or by differentiating the information, and extracting and imaging only a portion where the linear absorption coefficient distribution (density) changes stepwise.

14 Claims, 11 Drawing Sheets

UNIFORM DENSITY OBJECT OF A
DISC SHAPE 180 mm IN DIAMETER
HAVING A VOID 10 mm IN
DIAMETER.

DIMENSION = $|(\vec{R_1}+\vec{r_1})-(\vec{R_2}+\vec{r_2})|$

FIG. 12

IMAGING METHOD OF X-RAY COMPUTERIZED TOMOGRAPHY AND APPARATUS FOR X-RAY COMPUTERIZED TOMOGRAPHY

BACKGROUND OF THE INVENTION (1) Field of the Invention

The present invention relates to an imaging method of X-ray computerized tomography (X-ray CT) and X-ray CT apparatus preferable especially for industrial utilization.

(2) Description of the Prior Art

Improvement of resolution and shortening of measuring time are technical objectives for X-ray CT apparatus. For improvement of the resolution, it is necessary to make reconstruction scanning meshes fine, and, accordingly, it is necessary to make pitches of translational movement of an object fine. Nevertheless, the maximum reconstruction mesh size available at the present is 1024×1024 and, consequently, it is impossible to take a X-ray CT of a large object with high resolution. For example, taking a X-ray CT of an object having 1 meter width with a resolution of 0.1 millimeter is impossible because, the reconstruction mesh size necessary for the above described example becomes 10000×10000. Further, if the resolution is improved exactly depending on a Radon transformation which is one of the theories of CT, the measuring time is increased in proportion to a square of the resolution. For example, if the resolution is improved twice, the measuring time becomes four times, and if the resolution is improved 10 times, the measuring time becomes 100 times. That means, the CT technique of the prior art is impossible for use to image the cross section of a large object with high resolution, or if performed, the projection time becomes very long.

One of the means to solve the above described problems is a method to reconstruct a region of interest (hereinafter called ROI) from penetration data through the ROI.

Problems of image reconstruction of ROI in prior art were, as disclosed in JP-A-58-46947 (1983) "X-ray CT Apparatus", encountered in a first CT scanning of whole object and subsequent reconstruction of image in the ROI from penetration data through the ROI. In accordance with the prior art described above, information from outside the ROI contained in a penetrating datum is determined and subtracted from previously obtained whole image datum, and, accordingly a, linear absorption coefficient distribution (density) can be correctly reconstructed. The problem of the above described prior art is in the necessity to perform CT scanning of whole object at least once.

When ROI is reconstructed from penetration data through the ROI, the image is not correctly reconstructed and a deformation in linear absorption coefficient distribution (density) is generated.

Needs of a CT for industrial utilization are mainly for detection of defects and size measurement. Accordingly, information on shape, that means, "an orbit of discontinuous points of the density" is important, and information on the density itself is not so important. If it requires only the information on shape, performing CT for a whole cross section of the object as the above described prior art is not necessary, but only collecting penetrating data through the ROI and reconstructing the ROI based on the data.

SUMMARY OF THE INVENTION (1) Objects of the Invention

The first object of the present invention is to take out an information on shape from a reconstructed image of ROI from data penetrated through the ROI.

The second object of the present invention is to provide an X-ray CT apparatus for collecting penetration data through a part of region including an ROI of a measuring object in a short time.

The third object of the present invention is to provide an X-ray CT apparatus for realizing highly precise measurement of a length between two points in an measuring object and a fine detection of a defect.

(2) Methods Solving the Problems

The first object of the present invention is realized by setting a threshold function, which is determined by a ratio of width of ROI to width of measuring object, to a reconstructed image having deformation in linear absorption coefficient distribution (density), and making the image information bi-values or tri-values etc. by using the threshold function. Otherwise, the first object of the present invention is realized by taking out portions wherein the linear absorption coefficient distribution (density) changes stepwise by repeating differential operations to the reconstructed image having deformation in a linear absorption coefficient distribution (density).

The second object of the present invention is realized by furnishing an apparatus for setting position and width of the ROI of the measuring object, an apparatus for determining relative rotating angles of the measuring object to radiation source-detectors, and an apparatus for regulating both a starting point and finishing point of translational scanning of the measuring object relative to the radiation source-detectors depending upon the position and width of the ROI and relative rotating angles of the measuring object to the radiation source detectors.

The third object of the present invention is realized by an operation comprising of designation of two positions for length measurement, performing CT at each designated position by ROI, and calculation of length from the two CT images obtained by the ROI, and of designation of a defect position, performing CT at the designated position by ROI, and the cross section image obtained by the ROI.

Operation of the method for realizing the first object of the present invention is explained hereinafter.

Data penetrating a ROI contains both information on the ROI and information on an outside region of the ROI. When image is reconstructed based on the above described data using conventional image reconstruction methods such as a filtered background projection method or a convolution method, deformation is generated in a linear absorption coefficient distribution (density) of the measuring object in the reconstructed image. Nevertheless, a shape as "an orbit of discontinuous points of the density" is correctly reconstructed. Accordingly, it is important to recognize shape information in the image reconstructed by the ROI, and to image the shape information.

On the other hand, in the reconstructed image by the ROI, the deformation of the linear absorption coefficient distribution (density) has a tendency to become more remarkable as the outside of the ROI becomes larger. Therefore, the linear absorption coefficient distribution (density) are changed to bi-values or tri-values, etc., by setting a threshold function in the linear absorption coefficient distribution (density) depending on the above described tendency, and then the shape information is determined. Otherwise, portions wherein information on the linear absorption coefficient distribution (density) are changed stepwise, namely shape information and are determined by repeating differential operations on the reconstructed image by the ROI (the image having deformation in the linear absorption coefficient distribution (density)).

In the manner described above, the apparatus related to the present invention can image the shape information from the reconstructed image by the ROI.

Operation of the method for realizing the second object of the present invention is explained hereinafter.

When a radiation source-detector system is fixed and the measuring object is operated with translation and rotation, a problem results in that a collection of data penetrating through a ROI is changing of both in terms of starting position and finishing position of the scanner in translation owing to change of positions of the ROI of the measuring object on a turn table at every rotation.

Accordingly, in an apparatus relating to the present invention, both a starting position and finishing position of the scanner in translation is regulated depending on position and width of the ROI of the measuring object and rotational angles of the turn table. Namely, a center of the turn table is placed at an original point of a measuring object coordinates system, the translational direction is placed on the y-axis, and center of the circular ROI is placed at (XROI, YROI), and radius of the circle is assumed as RROI. Then, the central position of the ROI after rotation of the turn table by an angle of 8 from the initial position becomes (XROI', YROI'). Where, the XROI' and YROI' are respectively expressed by the following equations:

$$XROI'=XROI \cdot \cos\theta - YROI \cdot \sin\theta$$

$$YROI'=XROI \cdot \sin\theta + YROI \cdot \cos\theta$$

According to a consideration that distance between the center of the ROI and the radiation source is changed at every rotation of the turn table and the X-ray beam is fan-shape, a range of the translation is changed at every rotation. The range of the translation s can be expressed by the following equation:

$$s=2 \cdot \{(L+XROI') \cdot \tan\phi + RROI/\cos\phi\}$$

Where, $\phi$ is ½ of a divergent angle of the fan-beam.

In accordance with the above explanation, data penetrating through the ROI can be thoroughly collected in a short time by furnishing a regulating apparatus for regulating translational position at every rotation.

Further, when the measuring object is scanned by translational and rotational operations with a fixed radiation source-detectors system, the ROI is moved to central portion of the turn table before the scanning of the measuring object, and the translation is performed in a translation range being determined based on the width of the ROI. In the above described case, regulation of the translation at every rotation of the turn table becomes unnecessary by a moving of the ROI of the measuring object to the central portion of the turn table.

Operation of the method for realizing the third object of the present invention is explained hereinafter.

When measuring a distance between two points in the measuring object, preciseness of the measurement depends on a width of a reconstructed mesh. For example, if the width of a the reconstructed mesh is in an order of centimeter, preciseness of the distance between the two points is also in the order of a centimeter. In order to measure the distance more precisely, a finer reconstructed mesh is necessary.

Accordingly, regions including each point for the distance measurement are assigned as ROI, and then, ROI CT is performed. In this case, the width of the reconstructed mesh in the two regions for the distance measurement has preciseness, for example, in the order of a millimeter. Further, the above described point can be said similarly on image display of defects.

Next, the case for measuring a length is explained hereinafter. The length is determined by the following equation based on the obtained cross section image:

$$length=|(R1+r1)-(R2+r2)|$$

Where, R1 and R2 are position vectors for measurement of the length between the two points settled at first, r1 and r2 are vectors for measurement of the length on the cross section obtained by the ROI CT, and the original point of each vectors are at R1 and R2.

DETAILED DESCRIPTION OF THE EMBODIMENTS (Embodiment 1)

Hereinafter, details of the present invention are explained referring to an embodiment.

Figure 3:
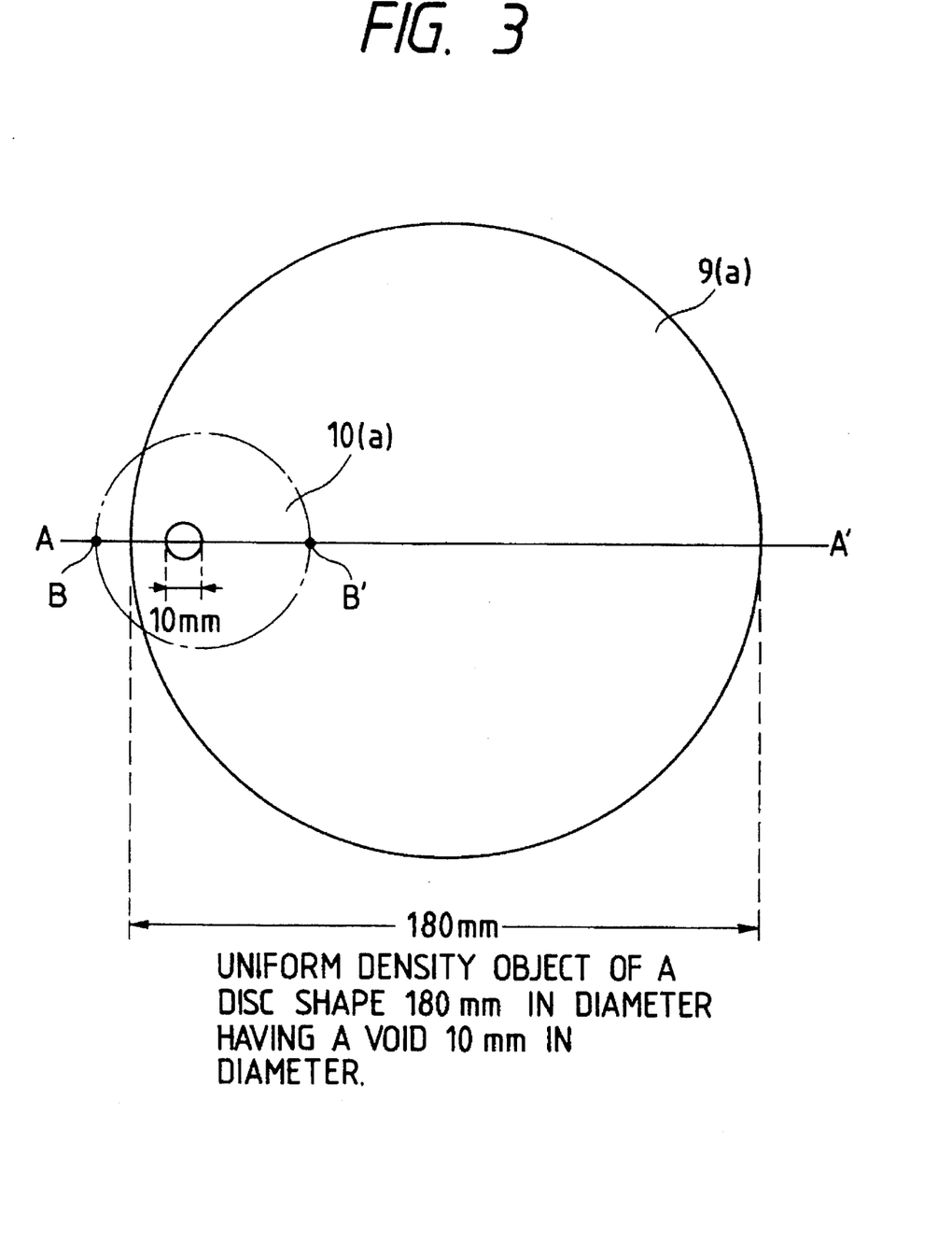
FIG. 3 is a schematic illustration indicating an example of measuring object and ROI, FIG. 4 (a), (b), and (c) are schematic illustration for explanation of the measuring object shown in FIG. 3 and of taking out the shape information from the reconstructed image in the ROI.

First, a relation between object to be measured (also known as "measuring object") 9(a) and its ROI 10(a) is indicated in FIG. 3. In FIG. 3, a disc having an uniform density and 180 mm in diameter as the measuring object 9(a) and a circular portion having a void of 10 mm in diameter as the ROI 10(a) are illustrated. The above numerals are examples giving a concept on the size of the object.

By careful watching of the ROI 10(a) in FIG. 3 in relation to information on penetration data, it is understood that the penetration data include information from both the ROI and outside the ROI. Namely:

(Information on penetration data)× (Information from the ROI)+ (Information from outside the ROI)

If images are reconstructed based on the above described penetration data by conventional image reconstruction methods such as a filtered back projection method and a convolution method, the information from outside the ROI can not be correctly canceled and remains in a the ROI 10(a). Accordingly, deformation in linear absorption coefficient distribution (density) of the measuring object 9(a) is generated in the reconstructed image. The deformation is generally related to width and density of the measuring object and width of the ROI. But, the shape as "an orbit of discontinuous points of density" is correctly reconstructed.

Therefore, the points of the present invention are in recognition of the shape information from the reconstructed image by the ROI and in imaging of the shape information.

On the other hand, there is a tendency in the deformation of the linear absorption coefficient distribution (density) in the reconstructed image by the ROI. The tendency is such that the linear absorption coefficient distribution (density) increases rapidly as moving toward an outside in the ROI. The tendency is more remarkable as the region outside the ROI is larger.

Figure 4:
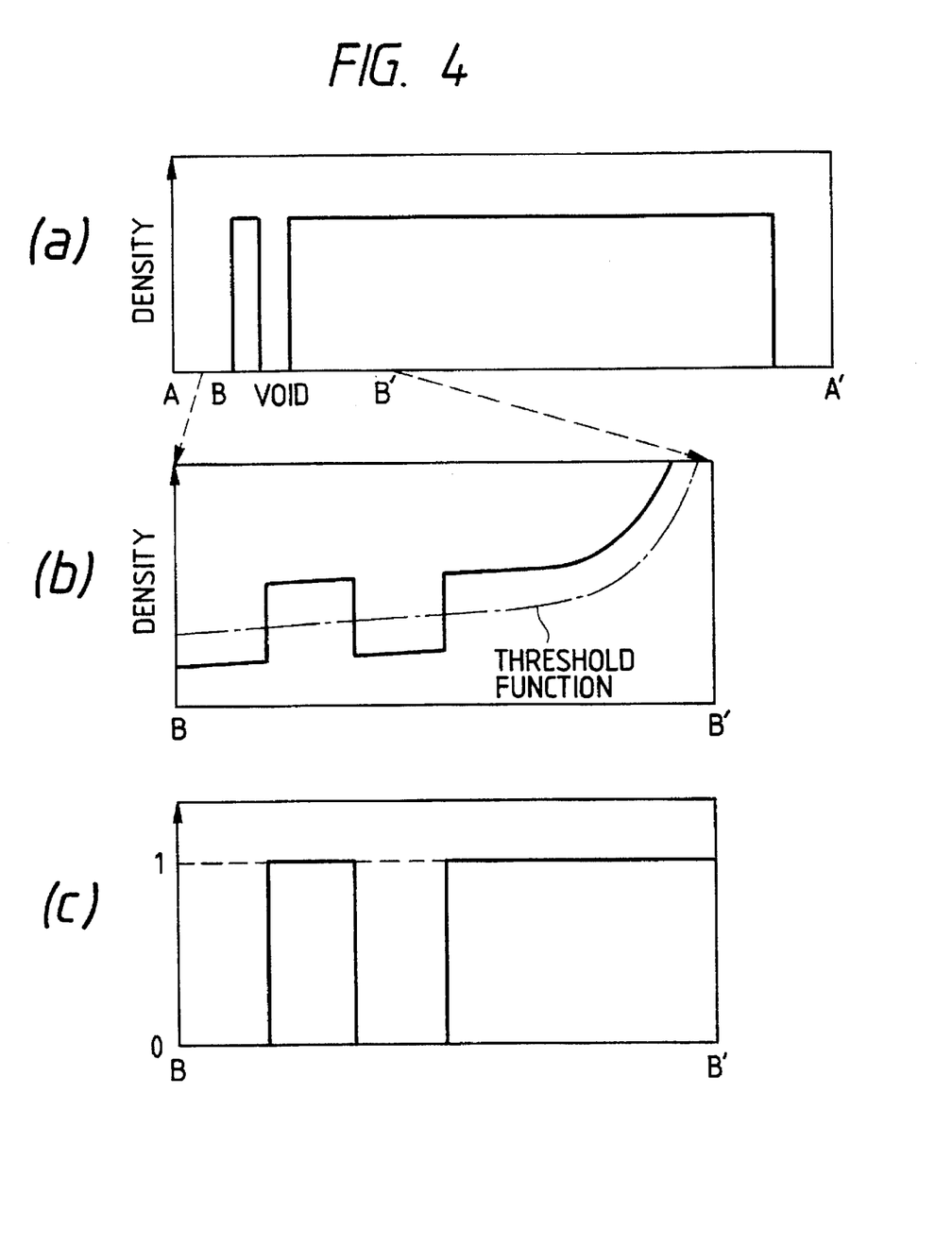

The above described situation is explained referring to FIG. 4.

FIG. 4(a) indicates the original linear absorption coefficient distribution (density) in the A–A' cross section of the measuring object 9(a), and FIG. 4(b) indicates the linear absorption coefficient distribution (density) in the A–A' cross section of the image wherein only B–B' cross section in the ROI 10(a) of the measuring object 9(a) is reconstructed. The deformation shown in FIG. 4(b) with a solid line is generated by the reconstruction. In the deformation, the linear absorption coefficient distribution (density) increases rapidly as moving toward an outside of the ROI, and linear absorption coefficients (density) is generated even in an air layer which originally does not have the linear absorption coefficient distribution (density). The above described tendency is with respect to deformation is general. In any way, the reconstructed image from the ROI 10(a) can not reproduce the original linear absorption coefficient distribution (density).

Accordingly, in the present invention, a threshold function is set in the linear absorption coefficient distribution (density) of the cross section image as shown in FIG. 4(b) with a one-dot chain line as an embodiment. Subsequently, the image is made to bi-values by giving 1 when the image datum is larger than the threshold function and zero when the image datum is smaller than the threshold function, and the shape information as shown in FIG. 4(c) is obtained.

Besides, the image may be made to not only bi-values but also tri-values, etc. Otherwise, as another embodiment, the shape information, namely a portion wherein the linear absorption coefficient distribution (density) change stepwise, can be obtained by repeating differential operations on the reconstructed image from the ROI (the image having deformation in the linear absorption coefficient distribution (density)).

Hereinafter, an operation principle of the CT apparatus relating to the present invention is explained.

Figure 1:
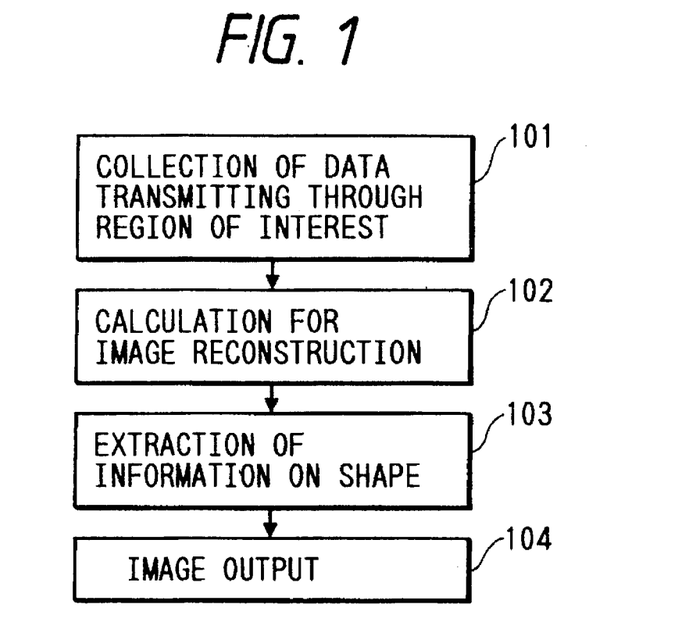
FIG. 1 is a whole flow chart of the present invention.

A whole flow chart of the CT apparatus relating to the present invention is indicated in FIG. 1. As for the first step, data on penetration of ROI in a measuring object are collected (101). A conventional CT apparatus requires collection of data covering a whole body of the measuring object, but, in accordance with the present invention, only the data on penetration through the ROI in the measuring object is required to be collected, and shortening of CT scanning time can be realized.

In the second step, the ROI is reconstructed from the collected data (102). As for image reconstruction methods, a conventional filtered back projection method or a convolution method are used.

In the third step, a shape information is obtained from the image reconstructed in the second step (103).

In the fourth step, a cross section image having only the shape information is put in an image output apparatus (104).

Figure 2:
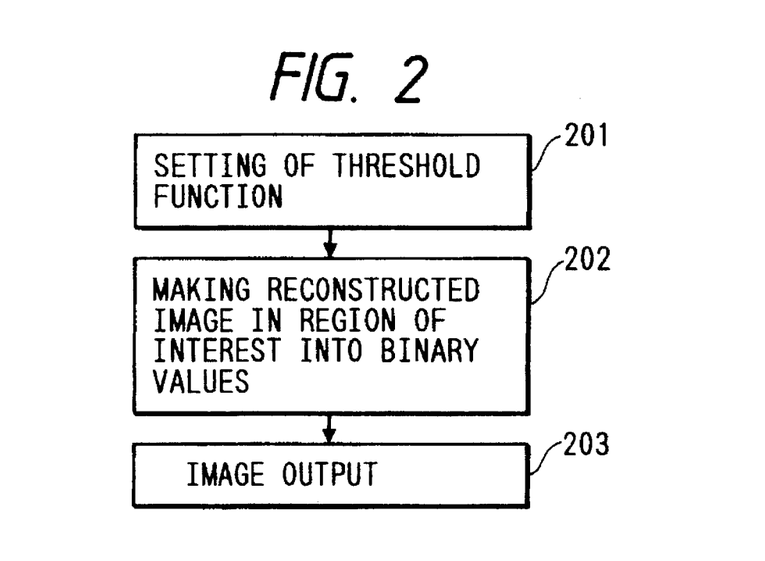
FIG. 2 is a flow chart for taking out shape information of the present invention.

A flow chart for obtaining the shape information relating to the present invention is indicated in FIG. 2.

In the first step, a threshold function is set depending on width of the measuring object and width and position of the ROI (201). The threshold function is set as a function of position in the image. That means, if giving S to the function, S can be represented by the following equation;

$$S=S(x,y)$$

Where, x, y indicate position coordinates in the image. If making to bi-values, only one threshold function is sufficient. If making to more than bi-values, a number of the threshold functions must be determined depending on number of the values.

In the second step, the reconstructed image of the ROI is made to bi-values, or tri-values, and so on depending on the threshold functions (202). In accordance with the operation, a shape information can be obtained from the image having deformation in linear absorption coefficient distribution (density).

In the third step, the image obtained in the second step is put in an image output apparatus (203).

As explained above, in accordance with the CT apparatus relating to the present invention, imaging of the shape information obtained from the reconstructed image by the ROI becomes possible. Further, the image is useful in such application fields wherein shape information is important as defect detection and dimensions measurement.

Next, explained is an X-ray CT apparatus for collecting data on penetration of ROI relating to the present invention.

Figure 5:
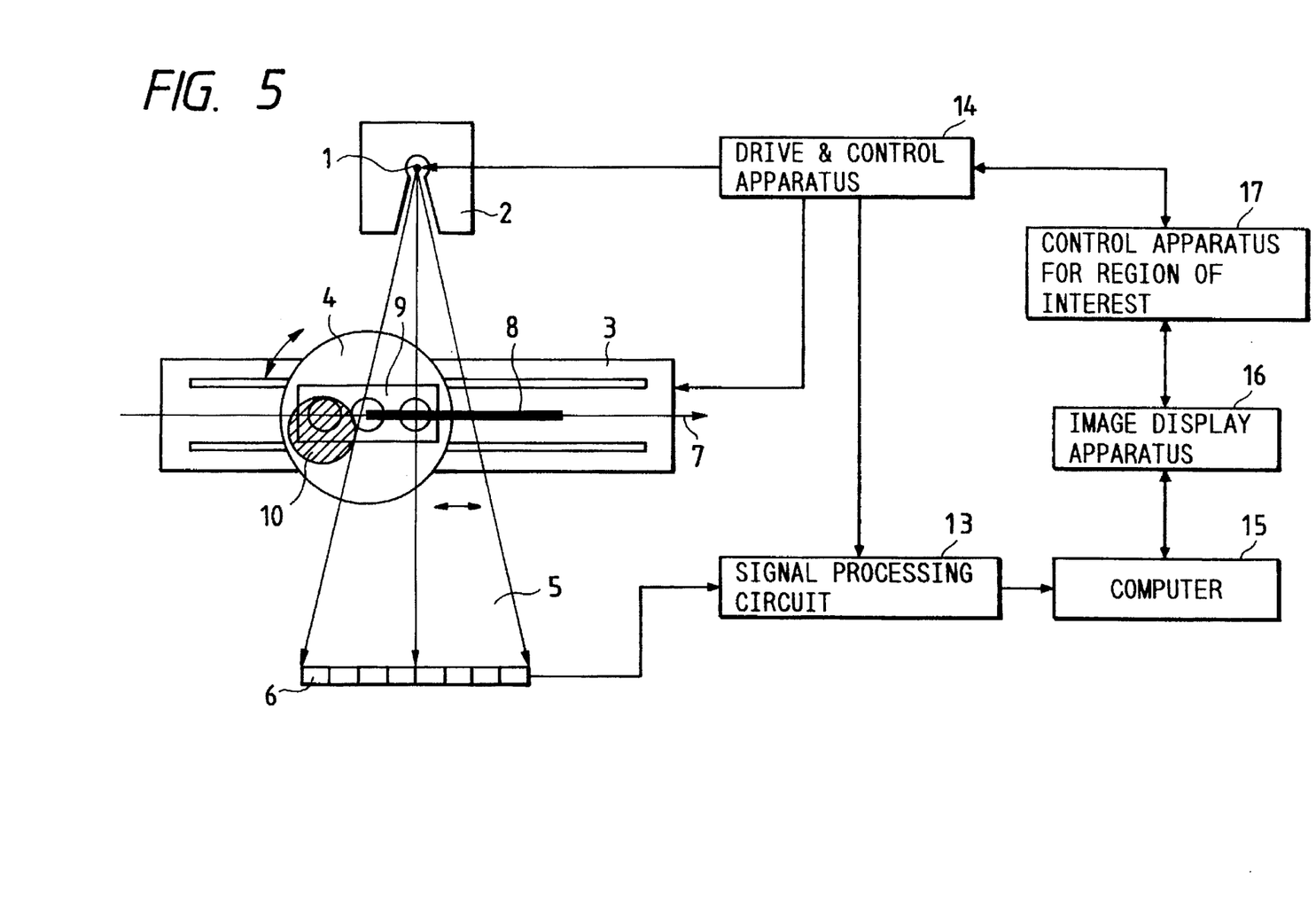
FIG. 5 is a schematic illustration indicating the composition of the X-ray CT apparatus in the first embodiment of the present invention.

The first embodiment of the apparatus is schematically indicated in FIG. 5. The respective numerals 1 is an X-ray source, 2 is a pre-collimator, 3 is a scanner, 4 is a turn table, 5 is fan-beam X-ray, 6 is detectors arranged in an array, 7 is a translational axis, 8 is a range of translation, 9 is a measuring object, 10 is ROI in the measuring object, 11 is a signal processing circuit, 14 is a driving control apparatus, 15 is a computer, 16 is an image display apparatus, and 17 is a ROI control apparatus.

Figure 6:
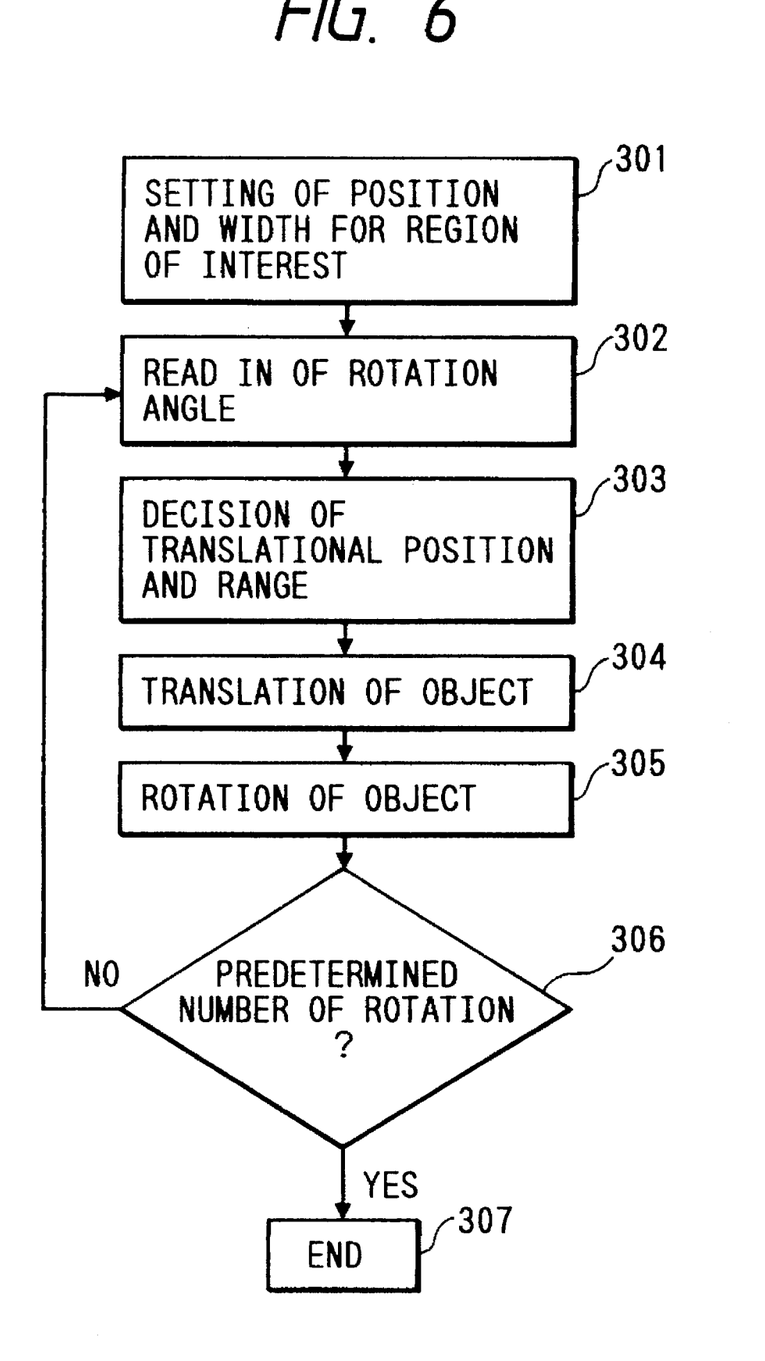
FIG. 6 is a flow chart of the first embodiment.

Referring to the flow chart in FIG. 6, operation of data collection in the present embodiment is explained.

First, position and width of the ROI 10 in the measuring object 9 are set (301), and an information on rotating angle of the turn table 4 is transferred from the driving control apparatus 14 to the ROI control apparatus 17 (302). Consequently, the position and the range 8 (the portion indicated with a broad line in FIG. 5) of the translation of the scanner 3 are determined (303). Next, X-ray is generated at the X-ray source 1, the X-ray is converted to the fan-beam X-ray 5 by the pre-collimator 2, and the fan-beam X-ray 5 is projected to the measuring object 9 fixed on the turn table 4. The X-ray penetrated through the measuring object 9 is detected by the detectors 6 arranged in an array, and is stored in a memory apparatus in the computer 15 through the signal processing circuit 13. At that time, the driving control apparatus 14 regulates the X-ray source 1, the scanner 3, and the signal processing circuit 13 so as to translate the measuring object 9 (304). After every translation, rotation is performed under regulation by the driving control apparatus 14 (305), and judgement whether predetermined rotation is achieved or not is performed (306). If the predetermined rotation is not achieved, an information on rotating angles of the turn table 4 is transmitted to the ROI control apparatus 17 from the driving control apparatus 4 (302), a position and the range 8 of the translation of the scanner is determined (303), and the translation is performed (304). A series of the above described operations is repeated until the rotation reaches predetermined cycles (307).

In the above described manner, data on the ROI are collected.

Calculation for the image reconstruction in only the ROI is subsequently performed by a filtered back projection method or a convolution method with the data on an the ROI and pre-collected data on air layer using the computer 15, and only the shape information is extracted from the reconstructed image and is put in an image display apparatus.

(Embodiment 2)

Figure 7:
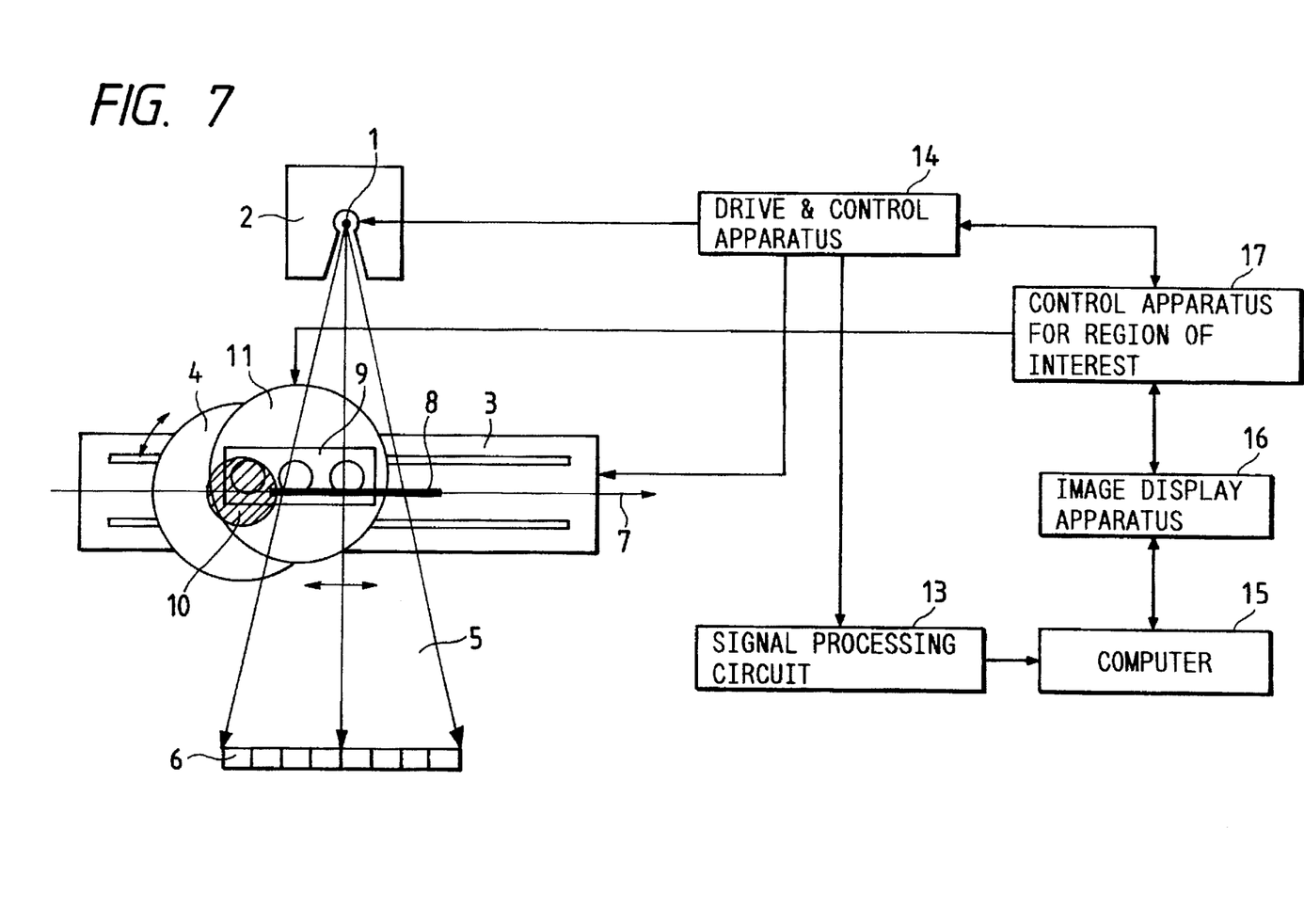
FIG. 7 is a schematic illustration of the second embodiment indicating modification of the first embodiment shown in FIG. 5.

The second embodiment of the present invention, which is a modification of the embodiment shown in FIG. 5, is illustrated in FIG. 7. The difference of the present embodiment from the embodiment shown in FIG. 5 is in installing the ROI center moving table 11 for moving the measuring object 9 to the center portion of the turn table 4.

Figure 8:
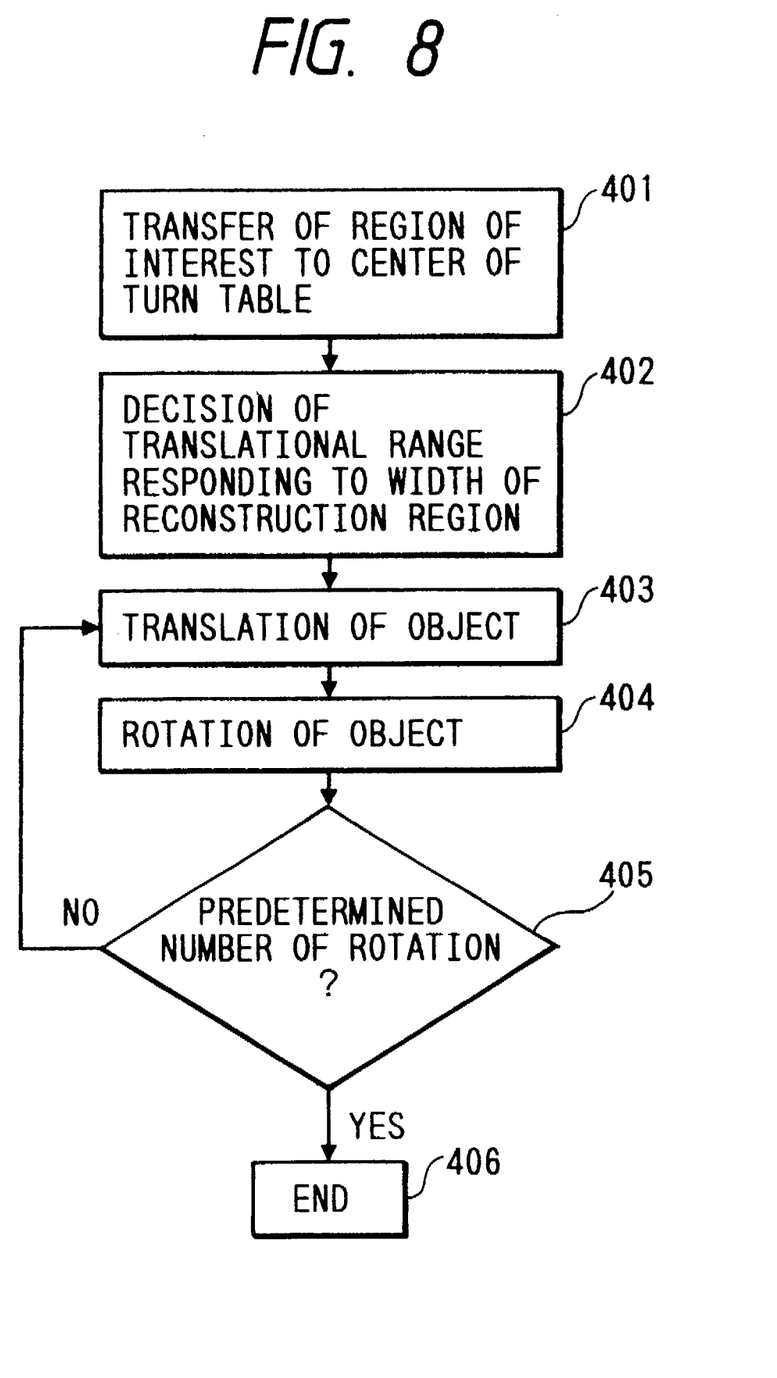
FIG. 8 is a flow chart of the second embodiment.

Referring to the flow chart in FIG. 8, operation of data collection in the present embodiment is explained.

First, position and width of the ROI 10 of the measuring object 9 are set in the ROI control apparatus 17, and the ROI 10 of the measuring object 9 moves to the center of the turn table 4 as shown in FIG. 7 (401). And, position and the range 8 (the portion indicated with a broad line in FIG. 7) of translation of the scanner 3 are determined depending on the width of the ROI of the measuring object 9 (402). Next, an X-ray is generated at the X-ray source 1, the X-ray is converted to the fan-beam X-ray 5 by the pre-collimator 2, and the fan-beam X-ray 5 is projected to the measuring object 9 fixed on the turn table 4. The X-ray penetrated through the measuring object 9 is detected by the detectors 6 arranged in an array, and is stored in a memory apparatus in the computer 15 through the signal processing circuit 13. At that time, the driving control apparatus 14 regulates the X-ray source 1, the scanner 3, and the signal processing circuit 13 so as to translate the measuring object 9 (403). After every translation, rotation is performed under regulation by the driving control apparatus 14 (404), and Judgement whether a predetermined rotation is achieved or not is performed (405). If the predetermined rotation is not achieved, the translation is performed (403). A series of the above described operations is repeated until the rotation reaches predetermined cycles (406).

In the present modified embodiment, control of the translation range 8 after every translation of the measuring object 9 is unnecessary because the ROI of the measuring object 9 moves to center portion of the turn table 4.

By the above described manner, data on the ROI are obtained, calculation for the image reconstruction is performed using the computer 15, and only the shape information is extracted from the reconstructed image, and the shape information is put in an image display apparatus as well as the embodiment shown in FIG. 5.

(Embodiment 3)

Figure 9:
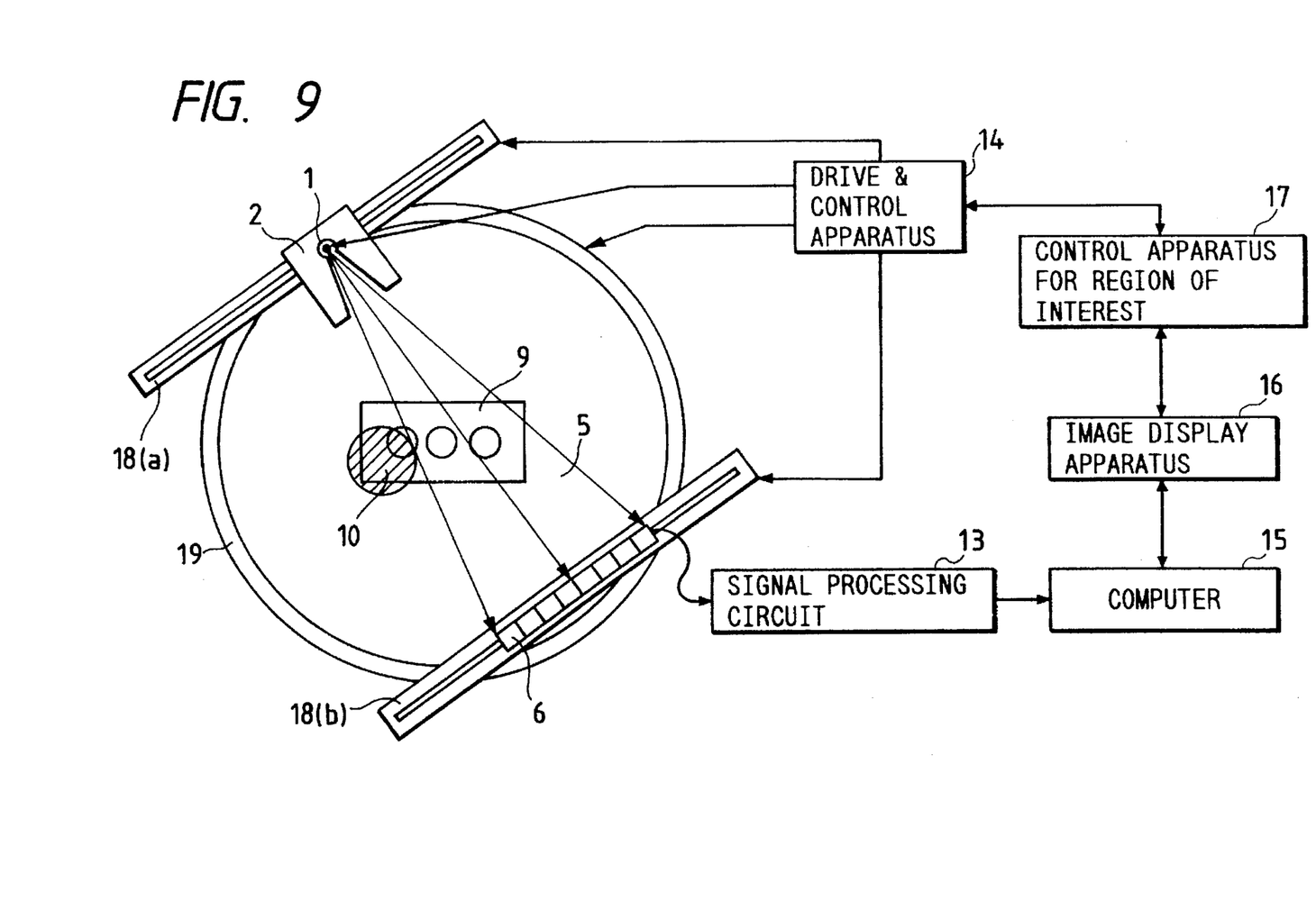
FIG. 9 is a schematic illustration of the third embodiment indicating modification of the first embodiment shown in FIG. 5.

The third embodiment of the present invention, which is a modification of the embodiment shown in FIG. 5, is illustrated in FIG. 9. The difference of the present embodiment from the X-ray CT apparatus shown in FIG. 5 is in installing the translational moving apparatus 18(a), (b) and the rotational moving apparatus 19, fixing the measuring object 9, integrating the X-ray source 1 with the detectors 6 arranged in an array into a body, and that the driving control apparatus 14 regulates the translational moving apparatus 18(a), (b) and the rotational moving apparatus 19 so as to make the integrated X-ray source 1 and the detectors 6 arranged in an array translate or rotate, and that the measuring object 9 is scanned translationally or rotationally. And, after every rotation, starting point and finishing point of the translation are regulated.

(Embodiment 4)

Figure 10:
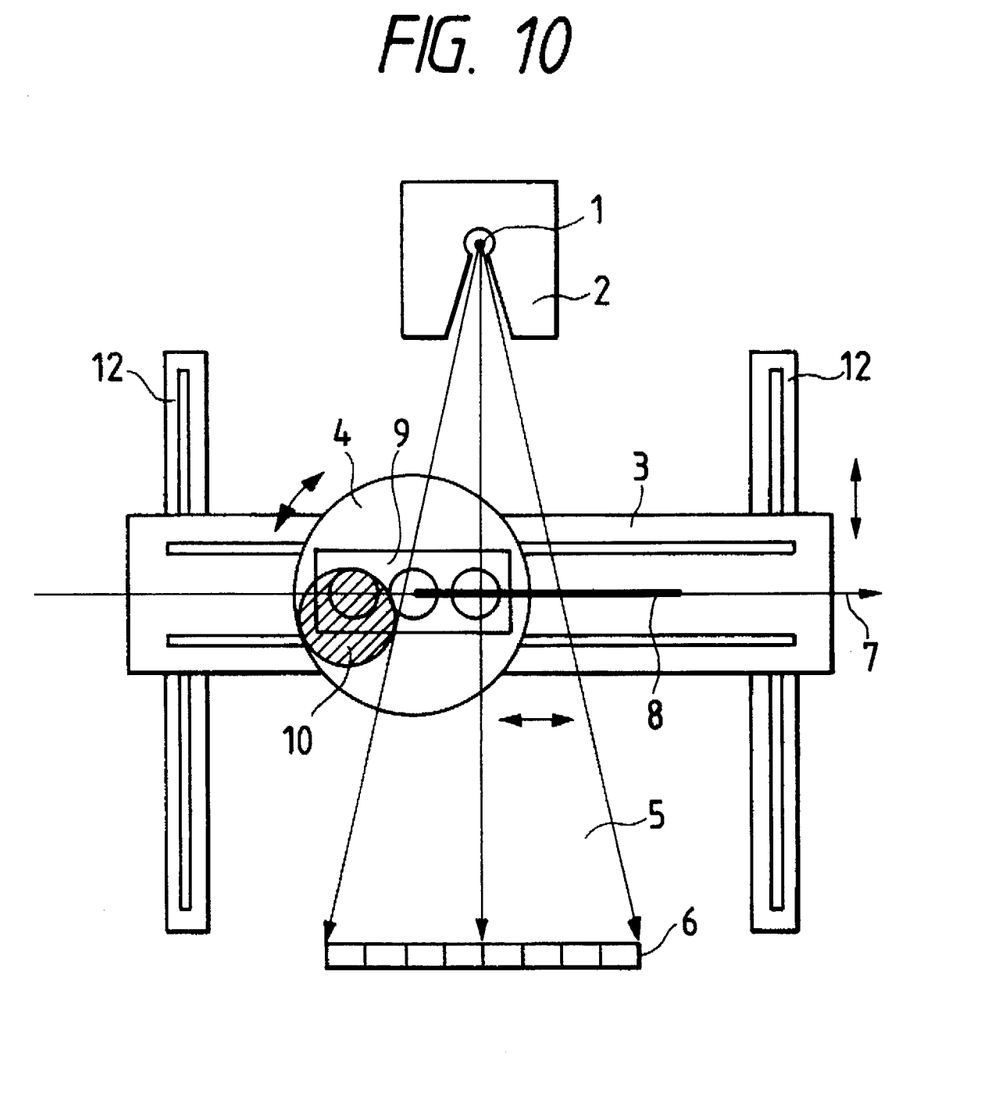
FIG. 10 is a schematic illustration of the fourth embodiment indicating modification of the first embodiment shown in FIG. 5.

The fourth embodiment of the present invention, which is a modification of the embodiment shown in FIG. 5, is illustrated in FIG. 10. The difference of the present embodiment from the X-ray CT apparatus shown in FIG. 5 is in installing the scanner moving apparatus 12, and that data on penetration of the ROI are collected by moving the measuring object translational axis 7 to the X-ray source 1 side or the detectors 6 arranged in an array side after every rotation of the turn table 4.

In the present embodiment, changing of the starting point and finishing point of the translation is unnecessary.

In accordance with the above described embodiments from 1 to 4, data on penetration of the ROI can be collected in a short time.

(Embodiment 5)

Figure 11:
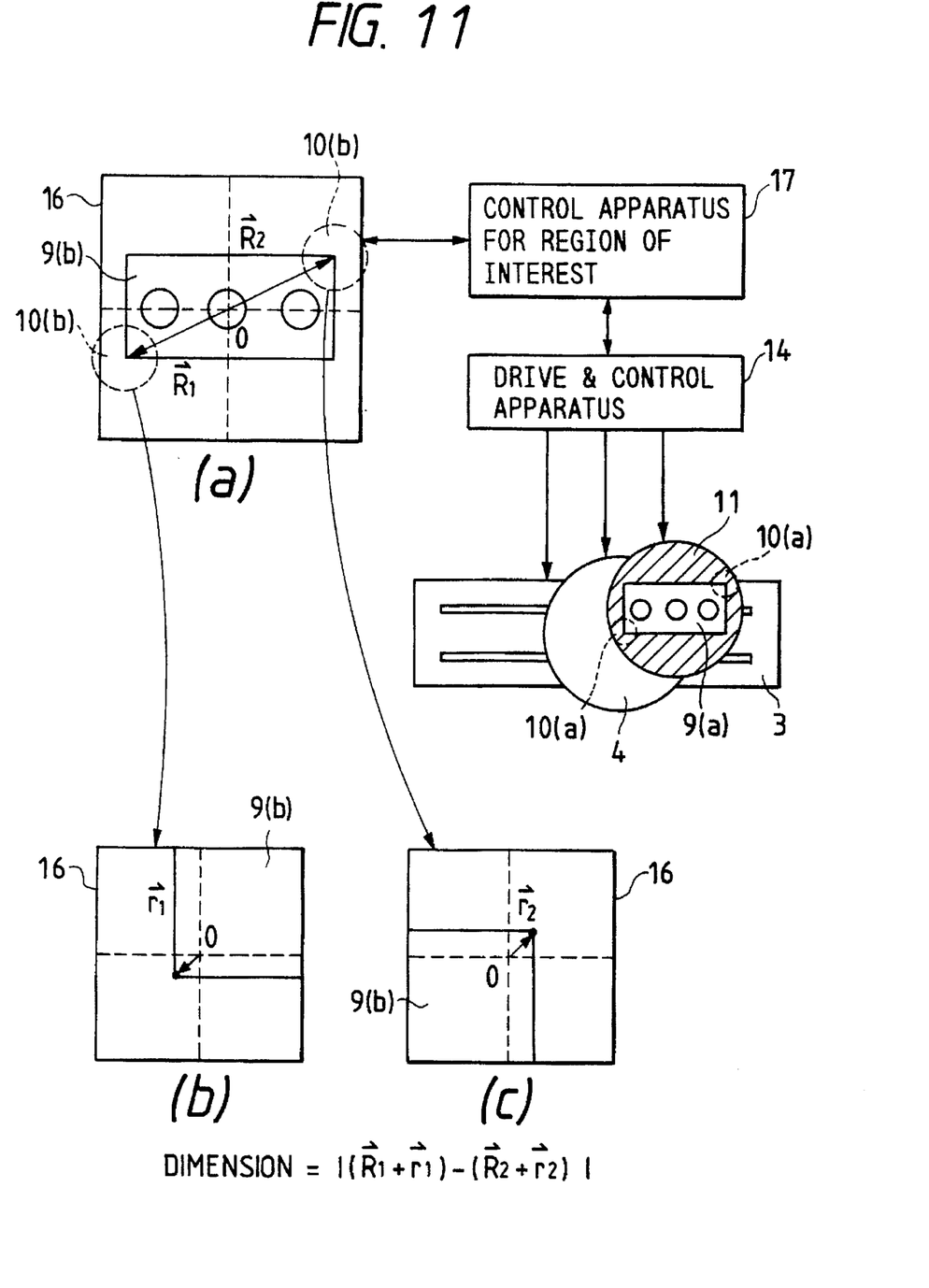
FIG. 11 is a schematic illustration indicating an embodiment of application of the present invention.

The fifth embodiment of the present invention shown in FIG. 11 is an example of the application of the present invention to measurement of a distance between two points on a measuring object.

In FIG. 11, each of the numerals indicate the following; 9(a)for the measuring object, 9(b) for the measuring object on the image, 10(a) for the ROI of the measuring object, and 10(b) for the ROI on the image. The scanner 3, the turn table 4, the center of the ROI moving table 11, the driving control apparatus 14, the image display apparatus 16, and the ROI control apparatus 17 are previously described.

First, the whole cross section image 9(b) at a cross section of the measuring object 9(a) is displayed on the image display apparatus 16 in such a manner as shown in (i) in FIG. 11. The operator designates points of which distance should be measured on the displayed image by using the ROI control apparatus 17. The designated points are assumed as two points in the ROI 10(b) on the image. In the above described case, resolution of the whole image of the cross section is in the order of a centimeter, and when the designated two points are assumed to have vectors R1 and R2 respectively to an original point on the image, preciseness of the vectors are also in the order of a centimeter.

Next, cross sectional CT are performed at the designated points as areas including each of the designated points as the ROI 10(a) in such a manner as shown in (ii) and (iii) using the CT apparatus of the present invention. In this case, resolution of the image becomes finer than the resolution for whole cross section because reconstruction is performed based on the ROI 10(a). For example, the resolution becomes in the order of a millimeter.

Again, points of which distance are to be measured are designated on the cross section images, (ii) and (iii), of the two ROI which are made in a manner described above, and are assumed as vectors r1 and r2. Preciseness of the vectors in this case are in the order of millimeter.

The distance between the two points can be calculated by the following equation:

$$Distance = |(R1+r1)-(R2+r2)|$$

With the above described present embodiment, a distance between two points can be measured more precisely, for example from the order of a centimeter to the order of millimeter, by using the CT apparatus of the present invention.

(Embodiment 6)

Figure 12:
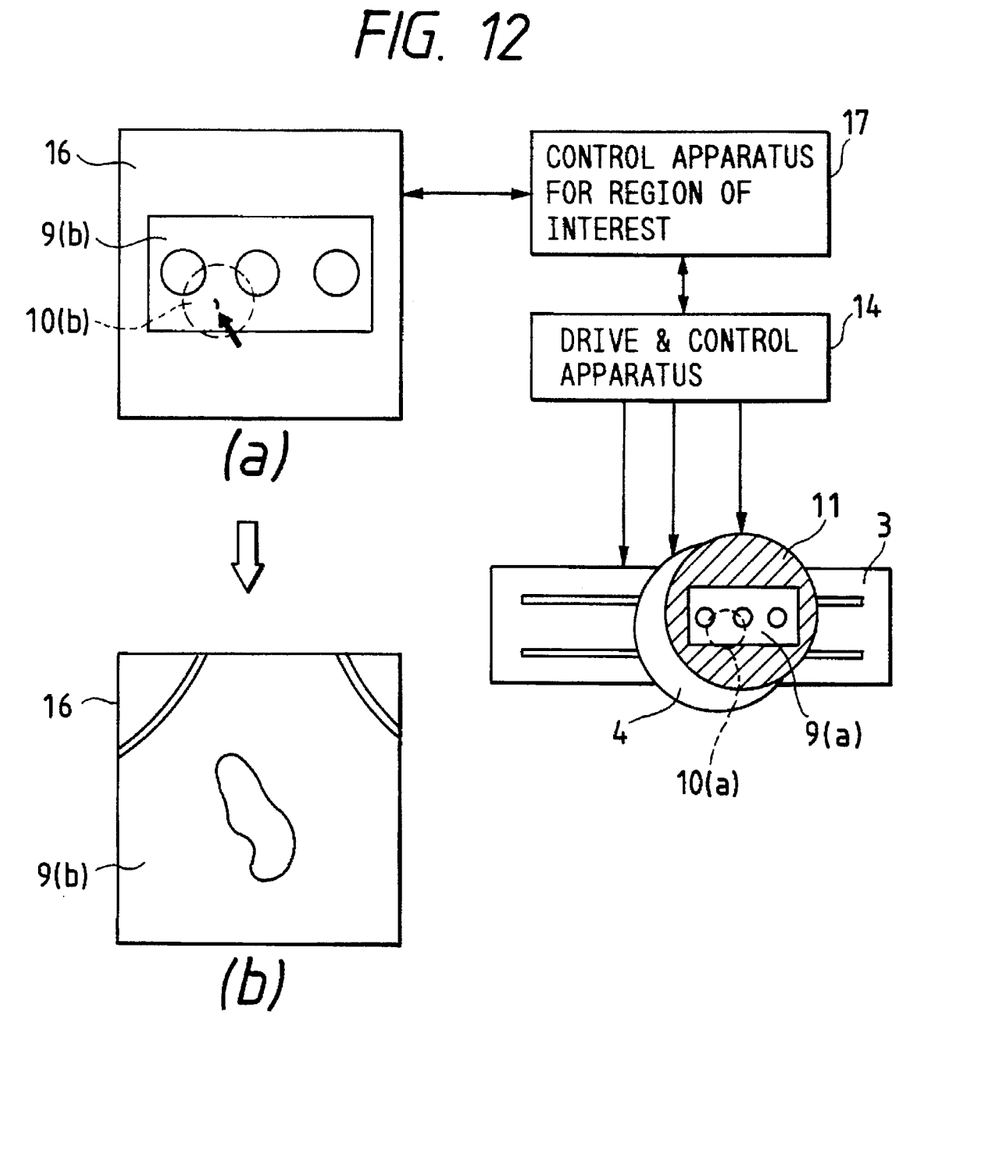
FIG. 12 is a schematic illustration indicating another embodiment of the application of the present invention.

The sixth embodiment of the present invention shown in FIG. 12 is another example of the application of the present invention for reconstruction of areas relating to defect portions of a measuring object. The same numerals as those in FIG. 11 indicate members having same composition.

First, the whole cross section image 9(b) at a cross section of the measuring object 9(a) is displayed on the image display apparatus 16 in such a manner as shown in (i) of FIG. 12 by cross section CT with a coarse resolution.

The defect portion indicated by an arrow in (i) of FIG. 12 can be recognized in the cross section image. If the operator wants to observe the defect portion with a finer resolution, the defect portion is designated as the ROI to the ROI control apparatus 17. Next, a cross section CT with a finer resolution is performed on the defect portion as the ROI 10(a) in a manner as shown in (ii) of FIG. 12.

As explained in the above embodiment, a cross section CT of the defect portion with a finer resolution can be performed by designating the defect portion as the ROI and using the CT apparatus of the present invention. Further, in the present embodiment, the operator designates the defect portion in the measuring object by himself, but automatic extraction of the defect portion can be performed by, for example, comparing the images having the defect portion and having no defect portion respectively.

In accordance with the present invention, a cross section CT with a high resolution can be performed in a short time without necessity to take a whole cross section CT at a cross section of the measuring object because a shape information is taken out from a reconstructed image of ROI based on data on penetration of the ROI in the measuring object.

Further, when collecting the data on penetration of the ROI in the measuring object, the data on penetration of the ROI can be collected thoroughly in a short item by installing an apparatus for controlling a translational position at every rotation of the ROI, or, initially moving the ROI to a center of the turn table.

Measurement of a distance between two points in the measuring object, or, detection of a defect portion in the measuring object can be performed by designating the two points and the defect portion as the ROI and performing a cross section CT with a high resolution.

As above explained, the present invention realizes a CT apparatus which can perform cross section CT in a short time with a high resolution.

What is claimed is:

1. An imaging method of X-ray computerized tomography (X-ray CT) for imaging shape information of a region of interest in an object to be measured, said method comprising the steps of:

reconstructing image information of a region of interest, said reconstructing being based on penetration data of said region of interest, setting at least one threshold function with respect to said image information, said at least one threshold function corresponding to a linear absorption coefficient distribution (density) of said object in said image information, converting said image information into a gray scale image using said threshold function, with the converted image having at least two levels, to extract a shape information from said image information, and imaging said shape information.

2. An imaging method of X-ray CT for imaging shape information of a region of interest in an object to be measured, said method comprising the steps of:

collecting data on penetration of a region of interest in a measuring object, reconstructing only image information of said region of interest, said reconstructing being based on data of said region of interest, setting at least one threshold function with respect to said image information, said at least one threshold function corresponding to a linear absorption coefficient distribution (density) of said object in said image information, converting said image information into a gray scale image using said threshold function, with the converted image having at least two levels, to extract a shape information from said image information, and imaging said shape information.

3. An imaging method as claimed in any of claims 1 and 2, wherein said image information of said reconstructing step corresponds to a linear absorption coefficient distribution (density) in said object to be measured, and said shape information is more specifically extracted within said reconstructing, setting and converting steps by the steps of:

setting said at least one threshold function with respect to said image information, said at least one threshold function being for defining one of hi-value and tri-value levels within said distribution, and making said image information into one of bi-values and tri-values based on said at least one threshold function.

4. An imaging method as claimed in any of claims 1 and 2, wherein said image information of said reconstructing step corresponds to a linear absorption coefficient distribution (density) in said object to be measured, and said shape information is extracted within said reconstructing, setting and converting steps by the steps of:

differentiating said image information corresponding to said linear absorption coefficient distribution (density), and converting only portions where said image information corresponding to said linear absorption coefficient distribution (density) is found in said differentiating step to change in a stepwise manner.

5. An imaging method as claimed in claim 2, wherein said collecting step includes the step of controlling both a starting position and a finishing point of translational scanning of said object to be measured depending on a position and width of a region of interest in said object to be measured and rotating angles of a turn table.

6. An imaging method as claimed in claim 2, wherein said collecting step includes the step of fixing said object to be measured to a fixing apparatus, performing both translational scanning and rotating scanning with an integrated X-ray source and detectors, and controlling both a starting position and a finishing point of said translational scanning of said object to be measured depending on a width and rotating angle of a region of interest in said object to be measured.

7. An imaging method as claimed in claim 2, wherein said collecting step includes the step of moving a region of interest of said object to be measured to a central portion of a turn table, and controlling a range of translation depending on a width of said region of interest.

8. An imaging method as claimed in claim 2, wherein said collecting step includes the step of moving a position of a translational axis of a turn table with respect to a radiation source side or detectors, and controlling a range of translation depending on a width of a region of interest and said position of said translational axis.

9. An imaging method as claimed in claim 2, wherein said collecting step includes the step of moving a region of interest in said object to be measured to an arbitrary position on a turn table, and controlling a range of translation depending on a width of said region of interest.

10. An X-ray CT apparatus for using imaging of shape information for measuring a distance between two points of an object to be measured, said apparatus comprising:

a designating apparatus for designating first and second points of said object to be measured of which a distance therebetween is to be measured in a whole CT image, a collecting apparatus for setting first and second regions of interest including said first and second points, respectively, and collecting penetration data of each of said first and second regions of interest, a reconstructing apparatus for reconstructing first and second image information of said first and second regions of interest, respectively, using collected said penetration data based on said penetration data of said first and second regions of interest, a means for setting at least one threshold function with respect to said first and second image information, said at least one threshold function corresponding to a linear absorption coefficient distribution (density) of said object in said first and second image information, an image outputting apparatus for converting said first and second image information into a gray scale image using said threshold function, with the converted image having at least two levels, to extract a shape information from said image information, and outputting said shape information as first and second shape images of greater resolution than said whole CT image, and a redesignating apparatus for redesignating said first and second points of which a distance therebetween is to be measured in said first and second shape images.

11. An X-ray CT apparatus for image display of shape information of a defect portion in an object to be measured, said apparatus comprising:

a designating apparatus for designating a defect portion in a CT cross section image corresponding to an entire cross-section of said object to be measured, a setting apparatus for setting a region of interest which includes said defect portion, a reconstructing apparatus for reconstructing image information of said region of interest by high spatial resolution based on penetration data of said region of interest, a means for setting at least one threshold function with respect to said image information said at least one threshold function corresponding to linear absorption coefficient distribution (density) of said object in said image information, and, a shape outputting apparatus for converting said image information into a gray scale image using said threshold function, with the convened image having at least two levels, to extract a shape information from said image information, and outputting said shape information as an image.

12. An X-ray CT apparatus for image display of shape information in an object to be measured, said apparatus comprising:

an apparatus allowing designation of a region of interest of said object to be measured in a CT cross section image which is displayed on an image display apparatus, a reconstructing apparatus for reconstructing image information of said region of interest based on penetration data of said region of interest, means for setting at least one threshold function with respect to said image information, said at least one threshold function corresponding to a linear absorption coefficient distribution (density) of said object in said image information, a converting apparatus for converting said image information into a gray scale image using said threshold function, with the converted image having at least two levels, to extract a shape information from said image information, and outputting said shape information as an image.

13. An imaging method of X-ray computerized tomography (X-ray CT) for imaging shape information of a region of interest in an object to be measured, said method comprising the steps of:

performing a selective X-ray CT scanning substantially limited to said region of interest in said object in order to obtain penetration data of said region of interest, reconstructing image information of said region of interest, said reconstructing being based on penetration data of said region of interest, setting at least one threshold function with respect to said image information, said at least one threshold function being set in correspondence with a linear absorption coefficient distribution (density) of said object in said image information, converting said image information into a gray scale image using said at least one threshold function, with the converted image having at least two levels, to extract a shape information from said image information, and imaging said shape information.

14. An imaging method of X-ray computerized tomography (X-ray CT) for imaging shape information of a region of interest in an object to be measured, said method comprising the steps of:

performing a selective X-ray CT scanning substantially limited to said region of interest in said object in order to obtain penetration data of said region of interest, reconstructing image information of said region of interest, said reconstructing being based on penetration data of said region of interest, setting at least one threshold function with respect to said image information, said at least one threshold function being set depending on a width of said object and a width and a position of said region of interest within said object, converting said image information into a gray scale image using said at least one threshold function, with the converted image having at least two levels, to extract a shape information from said image information, and imaging said shape information.

* * * * *